US007611545B2

(12) United States Patent
Guerin et al.

(10) Patent No.: US 7,611,545 B2
(45) Date of Patent: Nov. 3, 2009

(54) COSMETIC ARTICLE AND PROCESS FOR DRY DYEING KERATIN MATERIALS

(75) Inventors: Frédéric Guerin, Paris (FR); Luc Gourlaouen, Asnieres (FR); Pascal Simon, Thiais (FR); Josselyne Raymonde Jacqueline Simon, legal representative, Thiais (FR)

(73) Assignee: L'Oreal S.A., Paris (FR)

( * ) Notice: Subject to any disclaimer, the term of this patent is extended or adjusted under 35 U.S.C. 154(b) by 77 days.

(21) Appl. No.: 12/000,598

(22) Filed: Dec. 14, 2007

(65) Prior Publication Data

US 2008/0244837 A1 Oct. 9, 2008

Related U.S. Application Data

(60) Provisional application No. 60/881,145, filed on Jan. 19, 2007.

(30) Foreign Application Priority Data

Dec. 14, 2006 (FR) .................................. 06 55519

(51) Int. Cl.
*A61Q 5/10* (2006.01)
(52) U.S. Cl. ..................... 8/405; 8/426; 8/490; 8/657; 8/675
(58) Field of Classification Search ...................... 8/405, 8/426, 490, 657, 675
See application file for complete search history.

(56) References Cited

FOREIGN PATENT DOCUMENTS

| DE | 10 2006 008 542 | 12/2006 |
| EP | 0 890 326 | 1/1999 |
| WO | WO 90/06745 | 6/1990 |
| WO | WO 2006/089806 | 8/2006 |
| WO | WO 2006/089806 A1 * | 8/2006 |
| WO | WO 2006/089807 | 8/2006 |
| WO | WO 2006/089809 | 8/2006 |

OTHER PUBLICATIONS

STIC Search Report dated Aug. 15, 2008.*
English language Abstract of DE 10 2006 008 542, dated Dec. 7, 2006.
English language Abstract of EP 0 890 326, dated Jan. 13, 1999.
French Search Report for FR 06/55519, dated Aug. 8, 2007.

* cited by examiner

*Primary Examiner*—Eisa B Elhilo
(74) *Attorney, Agent, or Firm*—Finnegan, Henderson, Farabow, Garrett & Dunner, L.L.P.

(57) ABSTRACT

The present disclosure relates to a substantially dry cosmetic article for dyeing keratin materials, comprising a porous flexible substrate, and at least one direct dyes and/or direct dye precursor in powder form, which are capable of dyeing the keratin material via heat transfer, the substrate and the direct dyes or direct dye precursors being non-covalently bonded to the substrate. Disclosed herein is also a method for dyeing keratin materials, for example, human keratin materials, via dry heat transfer, using the dry heat-transfer cosmetic article.

23 Claims, No Drawings

COSMETIC ARTICLE AND PROCESS FOR DRY DYEING KERATIN MATERIALS

This application claims benefit of U.S. Provisional Application No. 60/881,145, filed Jan. 19, 2007, the contents of which are incorporated herein by reference. This application also claims benefit of priority under 35 U.S.C. § 119 to French Patent Application No. FR 0655519, filed Dec. 14, 2006, the contents of which are also incorporated herein by reference.

The present disclosure relates to a cosmetic article for dyeing keratin materials, such as human keratin materials, via dry heat transfer. The disclosure further relates to a process for dyeing keratin materials, such as human keratin materials, via dry heat-transfer using said cosmetic article. The disclosure thus relates to the field of dyeing human keratin fibers, such as the hair.

It has been known for a long time how to modify the color of the hair, for example, how to mask white hairs. Two types of techniques for dyeing human keratin fibers are most commonly used.

The first method, known as direct or semi-permanent dyeing, comprises changing or providing color by applying a colored molecule that penetrates diffusively into the fiber and/or remains adsorbed on its surface.

The second method, known as oxidative dyeing or permanent dyeing, comprises changing or providing color by performing, inside the fiber itself, an oxidative condensation of dye precursors, which are uncolored or sparingly colored compounds. After this reaction, the dyes formed are insoluble and are trapped inside the fiber.

The two methods summarized above allow access to a wide range of colors.

A dye composition may be in various forms, such as a lotion, a mousse, a cream or a gel. However, most of these forms may have the drawback of running onto the face or onto other areas that it is not desired to dye. Furthermore, the use of these products may sometimes soil clothing, hairstyling accessories (combs, towels, etc.), basins, etc.

Moreover, the duration of the dyeing process may be long. The reason for this is that, after the leave-on time of the dye composition, it is necessary to rinse the hair thoroughly, or even to perform a shampoo wash, and to dry it.

Finally, the use of certain dyes that afford advantageous dyeing performance on the fibers is occasionally limited because of their poor solubility in aqueous formulation supports.

Accordingly, it would be desirable to find methods for dyeing human keratin materials that allow effective colorations to be obtained without one or more of the drawbacks mentioned above.

In French Patent Application Nos. 0 502 034, 0 502 030 and 0 502 031, it has been shown that it is possible to dye the hair using dyeing powders via heat transfer. For example, it has been demonstrated that certain direct dyes can color the hair simply by transferring dye from a dry composition onto the hair under the action of the temperature, without using a liquid vehicle support. Moreover, because the dye is initially used in solid form, there is no need either for rinsing or for shampooing and/or drying of the keratin fibers. Finally, since the heat transfer is rapid (a few minutes), the leave-on times are short.

This novel dyeing technique via dry heat transfer uses a dye composition that is in the form of a dry polymer film containing a dispersion of one or more dyes, deposited on a non-porous solid substrate (aluminium, plastic, etc.). However, this route for manufacturing dry films by dissolving the film-forming polymer in aqueous-alcoholic medium and then dispersing the dyes, spreading this preparation as a thin layer onto the solid substrate and finally drying, is long and may have problems in terms of solubility, formulation and/or drying time. Furthermore, the compositions provided in this form may not be easy to use, since the solid substrate can be too rigid and sparingly conformable. It would thus be desirable to have available an article that is easier to prepare and to use and that allows better contact with the fiber.

The present inventors have discovered a simpler method, which is very easy to perform, for dyeing the hair via heat transfer.

Thus, the present disclosure, in at least one embodiment, relates to a substantially dry cosmetic article for dyeing keratin materials, such as human keratin fibers, for example, the hair, comprising
    a porous flexible substrate, and
    at least one direct dye and/or direct dye precursor in powder form, which are capable of dyeing the keratin material via heat transfer,
    wherein the direct dye or direct dye precursor is non-covalently bonded to and/or in the substrate, and
    wherein the porous flexible substrate is chosen from nonwoven fibrous substrates and cellulose substrates of foam type.

Another aspect of the present disclosure relates to a process for dyeing keratin materials, such as human keratin fibers, e.g., the hair, using this article via dry heat transfer of these dyes or dye precursors.

The cosmetic article, as disclosed herein, is a dry article, i.e., during its use, it is never brought into contact with a liquid and it comprises no adhesive for bonding the coloring agent to the support.

The articles disclosed herein are prepared by impregnating the porous flexible substrate with powders of direct dyes or direct dye precursors, directly and without solvent. This has the advantage of not requiring the use of a liquid formulation support for the dye, which limits soiling during the dyeing operation. Furthermore, the fact that the dyes are used directly in their solid form makes it possible to use dyes that are sparingly soluble or sparingly stable in standard dyeing media. This may contribute towards further broadening the range of possible colors and/or towards obtaining faster colors.

As used herein, "substantially dry" is understood to mean that it comprises less than 5% by weight of water relative to the weight of the article.

As used herein, "non-permanently bonded" is understood to mean non-covalently bonded.

As used herein, "human keratin materials" is understood to mean keratin fibers, such as the hair and the eyelashes.

Unless otherwise indicated, the limits delimiting a range of values form part of this range.

The porous flexible substrate is more generally known as a wipe. Wipes for example, cosmetic wipes, are generally comprised of a substrate made of a material of natural or synthetic origin, which is, for instance, nonwoven, but which may also be a foam or fabric, the substrate being impregnated with a composition suited for the intended application. These wipes are commonly used and are appreciated for their practical aspect since they are disposable and are impregnated with the necessary and sufficient amount of cleansing or treating product.

As disclosed herein, the porous flexible substrates are, for example, woven or nonwoven fibrous substrates or cellulose substrates of foam type. As used herein, "flexible" is understood to mean thin supports, ranging from 0.5 mm to 20 mm, for example, ranging from 1 mm to 3 mm thick, which can easily follow the contours of the surface to be treated. The thin supports may, for example, be easily rolled up around a lock of hair.

The materials constituting these substrates are chosen such that the article withstands the temperature required for the heat transfer of the dyes onto the hair without degradation of the substrate. For example, nonwoven substrates, constituted of non-hot-melt natural fibers, linked together by means of techniques not involving chemical binding agents that risk melting during the heat transfer of the dyes may be used in at least one embodiment. Techniques that may be mentioned include, but are not limited to, hydrobonding or needle-bonding, the web of fibers having been made before hand by carding or via an aerodynamic route ("airlaid"). As used herein, "non-hot-melt natural fibers" is understood to mean fibers which keep their bodily integrity under heat, for example, during the heat transfer, which they will incur according to the present disclosure. Non-limiting examples of natural fibers that may be mentioned include silk fibers and cellulose fibers. Non-limiting mention may also be made of cellulose fibers that include wood pulp fibers, cotton fibers, jute fibers and flax fibers, and combinations thereof. Synthetic fibers may also be used, for instance, cellulose ester (cellulose acetate) fibers, viscose, polylactic acid fibers or polyamide fibers.

As disclosed herein, the direct dyes or direct dye precursors in powder form may be used alone or as a mixture with other types of powder. The particle size of these powders generally ranges from 0.1 to 100 μm, for example, ranging from 0.5 to 60 μm.

These direct dyes or direct dye precursors may be used in unmodified form or in the form of microcapsules containing direct dyes or direct dye precursors.

According to at least one embodiment of the present disclosure, the direct dyes or the direct dye precursors are chosen from compounds with a heat of vaporization of less than or equal to 200 KJ/mol.

These dyes may be nonionic, cationic or anionic.

Non-limiting examples of suitable dyes that may be used include acridine, acridone, anthranthrone, anthrapyrimidine, anthraquinone, azine, azo, azomethine, methine, benzanthrone, benzimidazole, benzimidazolone, benzindole, benzoxazole, benzopyran, benzothiazole, benzoquinone, bisazine, bis-isoindoline, carboxanilide, coumarin, cyanin (for instance azacarbocyanin, diazacarbocyanin, diazahemicyanin, hemicyanin or tetraazacarbocyanin), diazine, diketopyrrolopyrrole, dioxazine, diphenylamine, diphenylmethane and dithiazine dyes, flavonoids such as flavanthrones and flavones, fluorindine and formazan dyes, hydrazones, such as aryl-hydrazone dyes, hydroxy ketone, indamine, indanthrone, indigoid and pseudo-iondigoid, indophenol, indoaniline, isoindoline, isoindoline, isoindolinone, isoviolanthrone, lactone, methine, naphthalimide, naphthanilide, naphtholactam, naphthoquinone, nitro-(hetero)aromatic, oxadiazole, oxazine, perilone, perinone, perylene, phenazine, phenothiazine, phthalocyanin, polyene/carotenoid, porphyrin, pyranthrone, pyrazolanthrone, pyrazolone, pyrimidinoanthrone, pyronine, quinacridone, quinoline, quinophthalone, squarane, stilbene, tetrazolium, thiazine, thioindigo, thiopyronine, triarylmethane and xanthene dyes, and mixtures thereof.

According to at least one embodiment of the present disclosure, the direct dye is chosen from:

an azomethine dye corresponding to formula (I) below:

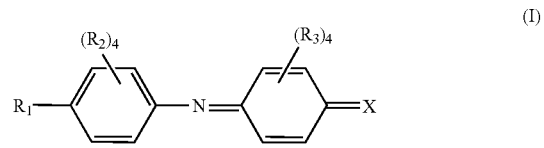

wherein:

$R_1$ is chosen from:
  a hydrogen atom;
  a hydroxyl group;
  an amino group; and
  an amino group mono- or disubstituted with one or two radicals, which may be identical or different, chosen from:
    $C_1$-$C_6$ alkyl radicals optionally substituted with a ($C_1$-$C_4$)-alkyl-$SO_2$NH group and a $NH_2$CO— group;
    ($C_1$-$C_6$)-alkyl-$O_2$SNH—($C_1$-$C_6$)-alkyl-NH— groups;
    ($C_6$)aryl($C_1$-$C_6$)alkyl groups;
    $C_6$ aryl groups; and
    ($C_1$-$C_4$)alkylpiperidine groups;
    wherein the radicals borne by the amino group may form, with the nitrogen atom to which they are attached, a 5- or 6-membered heterocycle optionally comprising a heteroatom chosen from oxygen and nitrogen;

$R_2$, which may be identical or different, is chosen from:
  hydrogen;
  linear or branched $C_1$-$C_6$ alkyl groups, optionally substituted with at least one group chosen from hydroxyl and $C_1$-$C_6$ alkoxy groups;
  $C_5$-$C_6$ cycloalkyl groups optionally substituted with at least one group chosen from hydroxyl and $C_1$-$C_6$ alkoxy groups;
  $C_1$-$C_6$ alkoxy groups;
  halogen atoms, for example, chlorine;
  cyano groups;
  ($C_6$)aryl($C_1$-$C_6$)alkyl groups; the aryl group being optionally substituted with at least one group chosen from hydroxyl, $C_1$-$C_6$ alkyl, and $C_1$-$C_6$ alkoxy groups;
  $C_6$ aryl groups optionally substituted with at least one group chosen from hydroxyl, $C_1$-$C_6$ alkyl, and $C_1$-$C_6$ alkoxy groups;
  ($C_1$-$C_6$)alkylcarbonyl groups;
  ($C_1$-$C_6$)alkylcarbonylamino groups;
  ($C_1$-$C_6$)alkylsulfonylamino groups;
  aminocarbonylamino groups;
  ($C_1$-$C_6$)alkylcarbonylamino groups;
  ($C_1$-$C_6$)alkylsulfoamino groups; and
  amino groups substituted with one or two radicals, which may be identical or different, chosen from $C_1$-$C_6$ alkyl, $C_1$-$C_6$ hydroxyalkyl and trifluoromethyl radicals;

$R_3$, which may be identical or different, is chosen from:
  hydrogen;
  halogen atoms, for example, chlorine;
  $C_1$-$C_6$ alkyl groups optionally substituted with at least one group chosen from hydroxyl and $C_1$-$C_6$ alkoxy groups;
  $C_1$-$C_6$ alkoxy groups;
  ($C_1$-$C_6$)alkylcarbonylamino groups;
  amino groups;
  amino($C_1$-$C_6$)alkylcarbonylamino groups;
  aminocarbonylamino groups;

($C_1$-$C_6$)alkoxycarbonylamino groups ($C_1$-$C_4$ aminoester alkyl); and aminocarbonyl groups wherein the amino group may be mono- or disubstituted with radicals, which may be identical or different, chosen from $C_1$-$C_6$ alkyl, $C_1$-$C_6$ haloalkyl, ($C_6$)aryl($C_1$-$C_6$)alkyl, $C_6$ aryl, ($C_1$-$C_6$)alkylcarbonylamino and ($C_1$-$C_6$)alkylsulfonylamino radicals, RaCONH— wherein Ra is chosen from a $C_1$-$C_4$ haloalkyl group, a ($C_6$)aryl($C_1$-$C_6$)alkyl group, a $C_6$ aryl group, a ($C_1$-$C_6$)alkoxy($C_1$-$C_6$)alkyl group, a $C_1$-$C_6$ hydroxyalkyl group, a cyano($C_1$-$C_6$)alkyl group, a methanesulfonamide group, a ($C_1$-$C_6$)alkylamino($C_1$-$C_6$)alkyl group, a substituted or unsubstituted $C_3$-$C_6$ cycloalkenyl group, a β-thienyl group, and one of the following groups:

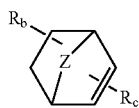 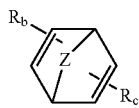 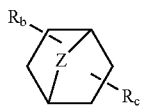

wherein Rb and Rc, independently of each other, are chosen from a hydrogen atom, a halogen atom and a $C_1$-$C_6$ alkyl chain, wherein Z is chosen from $CH_2$, O, S and NRd, wherein Rd is a hydrogen atom or a $C_1$-$C_6$ alkyl chain;

two radicals $R_3$ borne by two adjacent carbon atoms may form a benzene ring optionally substituted with a substituent chosen from a halogen atom, a $C_1$-$C_6$ alkyl group, an amino group and an amino group mono- or disubstituted with a $C_1$-$C_6$ alkyl or $C_1$-$C_6$ hydroxyalkyl radical; and X is an oxygen atom or an NH group;

an anthraquinone radical of formula (II) below:

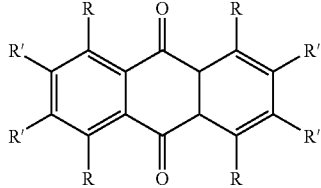

wherein:

R, independently of each other, are chosen from:
hydrogen;
hydroxyl;
amino groups; and
amino groups mono- or disubstituted with one or two radicals, which may be identical or different, chosen from $C_1$-$C_6$ alkyl, $C_1$-$C_6$ hydroxyalkyl and $C_6$ aryl radicals optionally substituted with at least one $C_1$-$C_6$ alkyl radical;

R', independently of each other, are chosen from:
hydrogen;
halogen;
hydroxyl;
amino groups;
amino groups mono- or disubstituted with one or two radicals, which may be identical or different, chosen from $C_1$-$C_6$ alkyl, $C_1$-$C_6$ alkylamino, $C_5$-$C_8$ cycloalkyl and ($C_1$-$C_6$)alkoxy($C_1$-$C_6$)alkyl radicals;

$C_6$ aryl radicals optionally substituted with at least one group, which may be identical or different, chosen from halogen atoms and $C_1$-$C_6$ alkyl, $C_1$-$C_6$ alkoxy and ($C_1$-$C_6$)alkoxy($C_1$-$C_6$)alkyl radicals;

($C_6$)aryloxy groups;

($C_6$)aryloxy groups substituted with a ($C_6$)aryl-$SO_3$ group, the aryl group being optionally substituted with at least one group, which may be identical or different, chosen from halogen atoms and hydroxyl, trifluoromethyl, $C_1$-$C_6$alkyl, $C_1$-$C_6$ alkoxy, $C_6$ aryl, ($C_6$)aryl($C_1$-$C_4$) alkyl, ($C_6$)aryloxy, nitro, $C_2$-$C_6$ acyl, ($C_2$-$C_6$)acylamino, ($C_1$-$C_6$)alkylmercapto, $C_6$ thiophenyl, sulfonyloxy and ($C_1$-$C_6$)alkylbenzenesulfonyl groups ($C_6$)aryloxy groups substituted with a group —$SO_2N(Ra)_2$ wherein Ra, which may be identical or different, is chosen from a hydrogen atom, a $C_1$-$C_6$ alkyl group, $C_2$-$C_6$ alkenyl group, ($C_6$)aryl($C_1$-$C_6$)alkyl group and a $C_5$-$C_8$ cycloalkyl radical, the two radicals Ra possibly forming, with the nitrogen atom to which they are attached, a 5- or 6-membered heterocycle;

a group —SRb wherein Rb is a 5- or 6-membered heterocycle, comprising the sulfur atom and optionally comprising a nitrogen, sulfur or oxygen atom;

COORc wherein Rc is chosen from a $C_1$-$C_4$ hydroxyalkyl group, ($C_1$-$C_4$)alkylphenyl group, $C_5$-$C_8$ cycloalkyl group, carbonyloxy($C_6$)aryl group and a carbonyl(C6) aryl group;

$SO_3$—($C_6$)aryl, the aryl radical being optionally substituted with at least group, which may be identical or different, chosen from halogen atoms and hydroxyl, trifluoromethyl, $C_1$-$C_6$ alkyl, $C_1$-$C_6$ alkoxy, $C_6$ aryl, ($C_6$) aryl($C_1$-$C_4$)alkyl, ($C_6$)aryloxy, nitro, $C_2$-$C_6$ acyl, ($C_2$-$C_6$)acylamino, ($C_1$-$C_6$)alkylmercapto, thiophenyl, sulfonyloxy and ($C_1$-$C_6$)alkylbenzenesulfonyl groups.

an azo dye corresponding to formula (III) below:

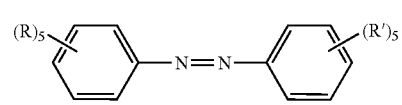

wherein:

R, which may be identical or different, and R', which may be identical or different, independently of each other, are chosen from:
hydrogen;
linear, branched or cyclic, saturated, unsaturated or aromatic $C_1$-$C_{30}$ hydrocarbon-based chains, optionally substituted with at least one halogen atom or with at least one group, which may be identical or different, chosen from the following groups: hydroxyl; nitro; cyano; carboxylic acid; allyl; haloallyl; $C_1$-$C_{10}$ alkoxy; ($C_1$-$C_4$) alkylcarbonylamino; ($C_1$-$C_4$)alkylaminocarbonyl; hydrogeno-carbonylamino; ($C_1$-$C_4$)alkylsulfonylamino; ($C_1$-$C_4$)alkoxycarbonylamino; ($C_1$-$C_4$)alkoxycarbonyl; ($C_1$-$C_4$)alkylcarbonyl($C_1$-$C_4$)alkoxycarbonyl; $CF_3$; amino; amino optionally substituted with at least one group, which may be identical or different, chosen from $C_1$-$C_{10}$ alkyl, $C_1$-$C_{10}$ hydroxyalkyl, $C_1$-$C_{10}$ alkoxyalkyl, $C_1$-$C_{10}$ aminoalkyl, (di)($C_1$-$C_{10}$)alkylamino($C_1$-$C_{10}$)alkyl, cyano($C_1$-$C_{10}$)alkyl, $C_6$-$C_{30}$ aryl, ($C_6$-$C_{30}$)aryl($C_1$-$C_4$)alkyl, ($C_4$-$C_{30}$)cyclo($C_1$-$C_{12}$)alkyl, ($C_1$-$C_4$)alkylcarbonyl, ($C_1$-$C_4$)alkylcarboxy($C_1$-$C_4$) alkyl, allyl, haloallyl; and optionally interrupted with or attached to the aromatic nucleus via at least one heteroatom or via a group comprising at least one heteroatom chosen from oxygen, sulfur and nitrogen;

groups chosen from: hydroxyl; $C_1$-$C_4$ alkoxy; carboxylic acid; amino; amino substituted with at least one radical, which may be identical or different, chosen from $C_1$-$C_4$ alkyl, $C_2$-$C_4$ alkenyl, cyano($C_1$-$C_4$)alkyl, $C_1$-$C_4$ hydroxyalkyl, $C_6$-$C_{30}$ aryl, ($C_6$-$C_{30}$)aryl($C_1$-$C_4$)alkyl, allyl, ($C_1$-$C_4$)alkoxy($C_1$-$C_4$)alkyl, ($C_4$-$C_{30}$)cyclo($C_1$-$C_{12}$)alkyl, ($C_1$-$C_4$)alkylcarbonyl, ($C_1$-$C_4$)carboxy($C_1$-$C_4$)alkyl, haloallyl, amino($C_1$-$C_4$)alkyl, (di)($C_1$-$C_4$)alkylamino($C_1$-$C_4$)alkyl, ($C_1$-$C_4$)alkylsulfonyl, ($C_1$-$C_4$) alkoxycarbonyl; halogen; allyl; hydrogenocarbonyl; trifluoromethyl; nitro; and cyano radicals it being understood that at least one of the radicals R or R' is a group chosen from hydroxyl; nitro; cyano; amino; amino optionally substituted with one or more radicals; and optionally, two radicals R borne by two adjacent carbon atoms or two radicals R' borne by two adjacent carbon atoms may form, with the aromatic ring bearing the carbon atoms to which each is attached, a fused nucleus of naphthalene type optionally substituted with an aminosulfonyl or ($C_1$-$C_4$)alkylaminosulfonyl group.

According to at least one embodiment of the present disclosure, the radical $R_1$ of formula (I) is chosen from:

a hydroxyl group;

an amino group;

an amino group mono- or disubstituted with one or two radicals, which may be identical or different, chosen from: $C_1$-$C_4$ alkyl optionally substituted with a ($C_1$-$C_4$) alkylSO$_2$NH group or an NH$_2$CO— group, the radicals borne by the amino group may form, with the nitrogen atom to which they are attached, a 5- or 6-membered heterocycle optionally comprising a heteroatom chosen from oxygen and nitrogen.

The radicals $R_2$ of formula (I), which may be identical or different, may be, in at least one embodiment, be chosen from:

hydrogen;

linear or branched $C_1$-$C_4$ alkyl groups;

$C_1$-$C_4$ alkoxy group; and halogen atoms, for example, chlorine.

The radicals $R_3$ of formula (I), which may be identical or different, may be, in at least one embodiment, be chosen from:

hydrogen, $C_1$-$C_6$ alkyl groups optionally substituted with at least one group chosen from hydroxyl and $C_1$-$C_6$ alkoxy groups, $C_1$-$C_4$ alkoxy groups, amino groups, ($C_1$-$C_6$)alkylcarbonylamino groups, ($C_1$-$C_4$)alkoxycarbonylamino groups, two radicals $R_3$ borne by two adjacent carbon atoms may form a benzene ring optionally substituted with at least one substituent chosen from a halogen atom, a $C_1$-$C_6$ alkyl group, an amino group and an amino group mono- or disubstituted with a $C_1$-$C_6$ alkyl or $C_1$-$C_6$ hydroxyalkyl radical.

In at least one embodiment of the present disclosure, the anthraquinone direct dye corresponds to formula (IIa) below:

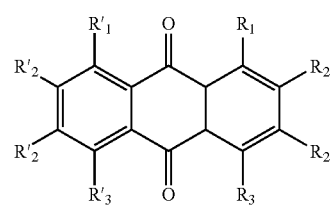

wherein:

$R_1$ is chosen from a hydrogen atom, a hydroxyl group, an amino group, and an amino group mono- or disubstituted with one or two radicals, which may be identical or different, chosen from $C_1$-$C_4$ alkyl, $C_1$-$C_6$ hydroxyalkyl and phenyl radicals optionally substituted with at least one $C_1$-$C_4$ alkyl radical;

$R'_1$ is chosen from a hydrogen atom, a hydroxyl group and an amino group;

$R_2$ and $R'_2$, independently of each other, may be chosen from hydrogen;

halogen atoms, for example, chlorine or bromine;

hydroxyl groups;

amino groups;

amino groups mono- or disubstituted with one or two radicals, which may be identical or different, chosen from $C_1$-$C_6$ alkyl, $C_1$-$C_6$ alkylamino, $C_5$-$C_8$cycloalkyl and ($C_1$-$C_6$)alkoxy($C_1$-$C_6$)alkyl radicals;

$C_6$ aryl radicals optionally substituted with at least one group, which may be identical or different, chosen from halogen atoms and $C_1$-$C_6$ alkyl, $C_1$-$C_6$ alkoxy and ($C_1$-$C_6$)alkoxy($C_1$-$C_6$)alkyl radicals;

($C_6$)aryloxy groups;

$R_3$ is chosen from a hydrogen atom, a hydroxyl group, an amino group, an amino group mono- or disubstituted with one or two radicals, which may be identical or different, chosen from $C_1$-$C_6$ alkyl, $C_1$-$C_6$ hydroxyalkyl and $C_6$ aryl radicals optionally substituted with one or more $C_1$-$C_6$ alkyl radicals;

$R'_3$ is chosen from a hydrogen atom, a hydroxyl group, and an amino group.

In at least one embodiment of the present disclosure, the anthraquinone direct dye of formula (II) is chosen from the following direct dyes: Disperse Blue 1 [2475-45-8], Disperse Blue 3 [2475-46-9], Disperse Blue 14 [2475-44-7], Disperse Blue 19 [4395-65-7], Disperse Blue 26 [3860-63-7], Disperse Blue 56 [31810-89-6], Disperse Orange 11 [82-28-0], Disperse Red 60 [17418-58-5], Disperse Violet 1 [128-95-0], Solvent Blue 35 [17354-14-2], Solvent Blue 59 [6994-46-3], Solvent Green 3 [17418-58-5], 6-methyl-1,3,8-trihydroxyanthraquinone (Emodine) [518-82-1], purpurin [81-54-9], quinalizarin [81-61-8], and mixtures thereof.

According to at least one embodiment, the azo direct dye corresponds to formula (IIIa) below:

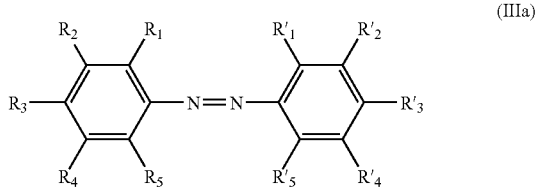

(IIIa)

wherein:
R'₁ is chosen from a hydrogen atom, an amino group and a hydroxyl group;
R'₂ is chosen from a hydrogen atom, a halogen atom, a carboxylic acid group, a $C_1$-$C_4$ alkyl group, a $C_1$-$C_4$ alkoxy group, an allyl group and an aminocarbonyl($C_1$-$C_4$)alkyl group;
R'₃ is chosen from a hydrogen atom, a hydroxyl group and a group of the type NR'₁R'₂ wherein R'₁ and R'₂ are chosen from, independently of each other, a hydrogen atom, a $C_1$-$C_4$ alkyl group, a $C_2$-$C_4$ alkenyl group, a cyano($C_1$-$C_4$)alkyl group, a $C_1$-$C_4$ hydroxyalkyl group, a $C_6$-$C_{30}$ aryl group, a ($C_6$-$C_{30}$)aryl($C_1$-$C_4$)alkyl group, an allyl group, a ($C_1$-$C_4$)alkoxy($C_1$-$C_4$)alkyl group, a ($C_4$-$C_{30}$)cyclo($C_1$-$C_{12}$)alkyl group, a ($C_1$-$C_4$)alkylcarbonyl group, a ($C_1$-$C_4$)alkylcarboxy($C_1$-$C_4$)alkyl group or a haloallyl group, a $C_1$-$C_4$ aminoalkyl group and a (di)($C_1$-$C_4$)alkylamino($C_1$-$C_4$)alkyl group;
R'₂ and R'₃ may form, with the benzene nucleus, a fused nucleus of naphthalene type optionally substituted with a group —SO₂—NHR wherein R is a hydrogen atom or an optionally substituted $C_1$-$C_4$ alkyl chain;
R'₄ is chosen from a hydrogen atom, a halogen atom, a hydroxyl group, a $C_1$-$C_4$ alkyl group, a $C_1$-$C_4$ alkoxy group and a ($C_1$-$C_4$)alkoxy($C_1$-$C_4$)alkyl group;
R'₅ is chosen from a hydrogen atom, a halogen atom, a hydroxyl group, an amino group, a $C_1$-$C_4$ alkyl group, a $C_1$-$C_4$ alkoxy group, a ($C_1$-$C_4$)alkylcarbonylamino group, a hydrogenocarbonylamino group, ($C_1$-$C_4$)alkylsulfonylamino, a ($C_1$-$C_4$)alkoxycarbonylamino group and a $CF_3$ group;
R'₄ and R'₅ may form, with the benzene nucleus, a fused nucleus of naphthalene type;
R₁ is chosen from a hydrogen atom, a halogen atom, a hydroxyl group, a nitro group and a cyano group;
R₂ is chosen from a hydrogen atom, a nitro group and a $C_1$-$C_4$ alkyl group;
R₃ is chosen from a hydrogen atom, a $C_1$-$C_4$ alkyl group, a $C_1$-$C_4$ alkoxy group, a ($C_4$-$C_{30}$)cyclo($C_1$-$C_{12}$)alkyl group, a $C_2$-$C_4$ alkenyl group, a ($C_1$-$C_4$)alkoxycarbonyl group, a ($C_1$-$C_4$)alkylcarbonyl group, a ($C_1$-$C_4$)alkoxycarbonyl($C_1$-$C_4$)alkoxycarbonyl group, ($C_1$-$C_4$)alkylcarbonyl($C_1$-$C_4$)alkoxycarbonyl, an aryl group, an amino group, a nitro group, a cyano group and a $CF_3$ group;
R₄ is a hydrogen atom or a nitro group;
R₅ is chosen from a hydrogen atom, a halogen atom, a carboxylic acid group, a hydroxyl group, an amino group, a cyano group and a $C_1$-$C_4$ alkyl group;

it being understood that at least one of the radicals R'₁ to R'₅ and R₁ to R₅ is a group chosen from hydroxyl, nitro, cyano, amino, amino optionally substituted with at least one radical.

According to at least one embodiment of the present disclosure, the radicals R'₁, R'₂, R₁, R₂ and R₄ of formula (IIIa), are hydrogen atoms.

In at least one further embodiment, the radical R'₃ of formula (IIIa) is chosen from a hydrogen atom and a group of the type NR''₁R''₂ wherein R''₁ and R''₂ are chosen from, independently of each other, a hydrogen atom, a $C_1$-$C_4$ alkyl group, a cyano ($C_1$-$C_4$)alkyl group, a $C_1$-$C_4$ hydroxyalkyl group and a $C_1$-$C_4$ aminoalkyl group.

In at least one further embodiment, the radical R'₄ of formula (IIIa) is a hydrogen atom.

In at least one further embodiment, the radical R'₅ of formula (IIIa) is a hydrogen atom or a $C_1$-$C_4$ alkyl group.

According to another embodiment, the radicals R'₄ and R'₅ of formula (IIIa) form, with the benzene nucleus, a fused nucleus of naphthalene type.

In at least one embodiment, the radical R₃ of formula (IIIa) is chosen from an amino group and a nitro group.

In at least one embodiment, the radical R₅ of formula (IIIa) is chosen from a hydrogen atom, a halogen atom, for example, chlorine or fluorine, and an amino group.

According to one non-limiting embodiment of the present disclosure, the azo direct dye of formula (IIIa) is chosen from the following direct dyes: Solvent Brown 1 [6416-57-5], Solvent Orange 1 [2051-85-6], Solvent Orange 7 [3118-97-6], Solvent Yellow 2 [60-11-7], Solvent Yellow 3 [97-56-3], Solvent Yellow 7 [1689-82-3], Solvent Yellow 14 [842-07-9], Disperse Orange 1 [2581-69-3], Disperse Orange 3 [730-40-5], Disperse Orange 25 [31482-56-1], Disperse Red 1 [2872-52-8], Disperse Red 13 [3180-81-2], Disperse Red 19 [2734-52-3], Disperse Red 50 [12223-35-7]+[40880-51-1], Disperse Yellow 3, Mordant Brown 4 [6247-28-5], Mordant Brown 6 [6247-28-5], Mordant Brown 24 [6370-46-3], Mordant Brown 48 [6232-53-7], Mordant Orange 1 [2243-76-7], Pigment Red 3 [2425-85-6], 4-dimethylamino-2-methylazobenzene [54-88-6], 2-(4-diethylaminophenylazo)benzoic acid [76058-33-8], N-ethyl-N-(2-aminoethyl)-4-(4-nitrophenylazo)aniline, N,N-hydroxyethyl-4-(4-nitrophenylazo)-2-methylaniline, N,N-hydroxyethyl-4-(4-aminophenylazo)-2-aniline, and mixtures thereof.

Precursors of these direct dyes may also be used, for example, the leuco forms.

Direct dyes or precursors of direct dyes capable of reacting with the amine functions present in keratin fibers, such as the hair, may also be used.

As disclosed herein, the direct dye(s) or direct dye precursor(s) used, may be present in an amount ranging from 0.5% to 50% by weight, for example, from 5% to 50% by weight relative to the total weight of the cosmetic article.

The powder compositions may comprise one or more cosmetic additives in powder form chosen from other cosmetic agents such as polymers (which may be hot-melt polymers), fragrances, preserving agents, pH agents, surfactants, screening agents, antioxidants, fatty substances, silicones, amino acids and any other adjuvant usually used in the dyeing of keratin materials.

In at least one embodiment, the content of additives in the powder may range from 0.01% to 20%; wherein the total content of additives, when they are present, does not exceed 80% by weight of the powder.

According to the process for preparing the cosmetic article disclosed herein, it is possible either to obtain a cosmetic article impregnated sparingly with colored or uncolored direct dye(s) or direct dye precursor(s), or to obtain a substantially colored article.

As used herein, "sparingly colored or uncolored" is understood to mean an article that has a difference in coloration before and after impregnation with the dye(s) or the precursor (s), wherein the difference is less than or equal to 10, this difference in color evaluated by the following equation:

$$DE=\sqrt{(L_i^*-L_0^*)^2+(a_i^*-a_0^*)^2+(b_i^*-b_0^*)^2}$$

wherein:

$L_i^*$, $a_i^*$, $b_i^*$ and $L_0^*$, $a_0^*$, $b_0^*$ are respectively, the colorimetric coordinates in the La*b* system of the fiber after and before impregnation, and the difference in chromaticity evaluated by the following equation:

$$DC=\sqrt{(a_i^*-a_0^*)^2+(b_i^*-b_0^*)^2}$$

wherein the difference is less than 5.

As used herein, "substantially colored" is understood to mean an article wherein the value DE defined above is greater than 5 and/or the difference in chromaticity is greater than 5.

In the context of substantially colored particles, the dyes used, in at least one embodiment, are the direct dyes of formulae (I), (II) and (III) described above and the dye precursors mentioned above.

The process for preparing the article may be any known dry impregnation process, for example, an impregnation process using an alternating electric field, cold plasma (0.1 to 20 kV/mm) after having sprinkled the direct dye or the direct dye precursor onto the porous flexible substrate. In at least one embodiment, it may not be necessary to perform a step of fixing the dyes or dye precursors.

This process is performed to obtain uniform distribution of the direct dye(s) or direct dye precursor(s) on and/or in the substrate.

In the context of the sparingly colored or uncolored articles, the impregnation is not followed by thermal fixing.

In the context of the substantially colored articles, the impregnation, in at least one embodiment, is followed by thermal fixing at a temperature ranging from 70 to 240° C. The optionally heat-fixed impregnated substrates may be covered with a protective film generally of polymeric nature.

The present disclosure further relates to a hair dyeing process using the above-disclosed article, the process comprising:

A strip of the powder-impregnated cosmetic article or nonwoven wipe may be cut to the desired size, this step being dependent on the shape and size of the available wipes.

The wipe is then positioned on either side of the keratin fibers, for example, a lock of hair. The wipe may, for instance, encircle or sandwich the lock of hair.

A heat source is then applied to the wipe, resulting in thermal transfer of the dye(s) onto the surface of and/or into the keratin materials.

As used herein, "thermal transfer" is understood to mean the application of heat to the dry composition placed in contact with or close to the keratin materials to be treated. This heat is obtained by means of a source at a temperature ranging from 100 to 500° C., for example, from 130 to 250° C. and further for example, ranging from 140 to 220° C.

The source of heat may be provided in a conventional manner, for instance, a hairdryer, a styling hood, a smoothing iron, a crimping iron, a pulsed or non-pulsed laser system (UV, visible or high-energy infrared light radiation), a system of heating tips, etc.

In at least one embodiment, this source of heat is placed in contact with the assembly of the wipe and the keratin materials to be treated.

The source of heat is applied to the wipe, for instance, a smoothing iron, for a time ranging from 1 second to 5 minutes, for example, ranging from 30 seconds to 3 minutes. The higher the temperature, the shorter the treatment time.

Without wishing to be bound by any theory, one of the possible mechanisms for the dyeing of the keratin materials may proceed via a step of vaporization or sublimation of the direct dye present in the dry composition.

Other than in the operating examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present disclosure. At the very least, and not as an attempt to limit the application of the doctrine of equivalents to the scope of the claims, each numerical parameter should be construed in light of the number of significant digits and ordinary rounding approaches.

Notwithstanding the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in its respective testing measurement.

The examples that follow are intended to illustrate the invention without being limiting in nature.

EXAMPLES

Composition:

The wipes of the invention were prepared from two 100% viscose nonwoven substrates (non-hot-melt fibres) below:

fine, relatively thin nonwoven of low basis weight: V 68 L Aquadim: Tharreau thick, thicker nonwoven of higher basis weight: VI 41 17C: Tharreau, and impregnated with the dyes Disperse Blue 3 or Disperse Red 60 via the cold plasma technique to a degree of impregnation of the dye powders (relative to the weight of the nonwoven) of, respectively, 10% for the thick nonwoven and 15% for the thin nonwoven.

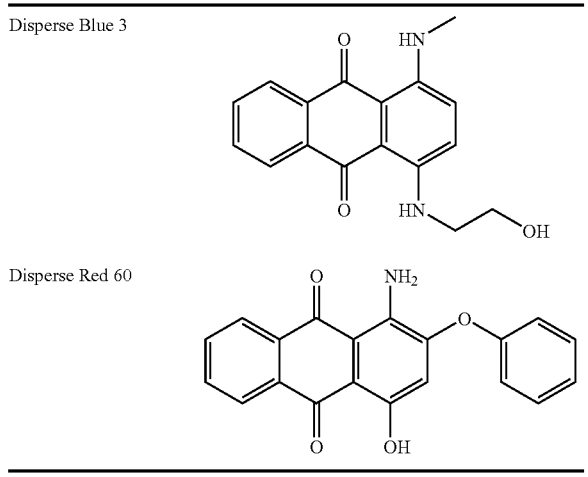

Disperse Blue 3

Disperse Red 60

Dyeing Process:

A strip of dye-impregnated nonwoven was cut to sizes of 5×9 cm and then positioned on either side of a lock of natural hair containing 90% white hairs, which has been spread out beforehand.

The smoothing iron was then applied for 5 minutes at 180° C.

Results:

The samples of nonwovens allowed color transfer onto the hair: fuchsia red for Disperse Red 60 and cyan blue for Disperse Blue 3.

What is claimed is:

1. A substantially dry cosmetic article for dyeing keratin materials, comprising
   a porous flexible substrate, and
   at least one direct dye and/or direct dye precursor in powder form and capable of dyeing the keratin material via heat transfer,
   wherein the substrate and the at least one direct dye and/or direct dye precursor is non-covalently bonded to and/or in the substrate, and
   wherein the porous flexible substrate is chosen from nonwoven fibrous substrates and cellular substrates of foam type.

2. The cosmetic article according to claim 1, wherein the article is obtained by a dry impregnation process.

3. The cosmetic article according to claim 2, wherein the article is obtained by a dry impregnation process using an alternating electric field.

4. The cosmetic article according to claim 1, wherein the thickness of the porous flexible substrate ranges from 0.5 mm to 20 mm.

5. The cosmetic article according to claim 1, wherein the porous flexible substrate is chosen from nonwoven substrates comprised of non-hot-melt natural fibers.

6. The cosmetic article according to claim 1, wherein the porous flexible substrate is chosen from silk fibers, cellulose fibers, wood pulp fibers, cotton fibers, jute fibers and flax fibers, and a combination thereof, cellulose ester fibres, viscose, polylactic acid fibres and polyamides fibres.

7. The cosmetic article according to claim 1, wherein the particle size of the powder of the at least one direct dye and/or direct dye precursor ranges from 0.1 to 100 μm.

8. The cosmetic article according to claim 1, wherein the at least one direct dye and/or direct dye precursor is chosen from compounds with a heat of vaporization of less than or equal to 200 KJ/mol.

9. The cosmetic article according to claim 1, wherein said at least one direct dye and/or direct dye precursor is nonionic, cationic or anionic.

10. The cosmetic article according to claim 9, wherein the at least one direct dye is chosen from acridine, acridone, anthranthrone, anthrapyrimidine, anthraquinone, azine, azo, azomethine, methine, benzanthrone, benzimidazole, benzimidazolone, benzindole, benzoxazole, benzopyran, benzothiazole, benzoquinone, bis-azine, bis-isoindoline, carboxanilide, coumarin, cyanin, diazine, diketopyrrolopyrrole, dioxazine, diphenylamine, diphenylmethane and dithiazine dyes, flavonoid, fluorindine, formazan, hydrazone, hydroxyketone, indamine, indanthrone, indigoid and pseudo-indigoid, indophenol, indoaniline, isoindoline, isoindoline, isoindolinone, isoviolanthrone, lactone, methine, naphthalimide, naphthanilide, naphtholactam, naphthoquinone, nitro(hetero)aromatic, oxadiazole, oxazine, perilone, perinone, perylene, phenazine, phenothiazine, phthalocyanin, polyene/carotenoid, porphyrin, pyranthrone, pyrazolanthrone, pyrazolone, pyrimidinoanthrone, pyronine, quinacridone, quinoline, quinophthalone, squarane, stilbene, tetrazolium, thiazine, thioindigo, thiopyronine, triarylmethane and xanthene dyes, and mixtures thereof.

11. The cosmetic article according to claim 9 wherein the at least one direct dye is chosen from:
an azomethine dye corresponding to formula (I) below:

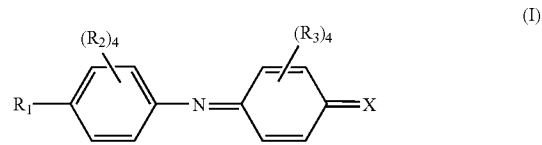

wherein:
$R_1$ is chosen from:
   a hydrogen atom;
   a hydroxyl group;
   an amino group;
   an amino group mono- or disubstituted with one or two radicals, which may be identical or different, chosen from:
      $C_1$-$C_6$ alkyl radicals optionally substituted with a ($C_1$-$C_4$)alkylSO$_2$NH group or an NH$_2$CO— group;
      ($C_1$-$C_6$)alkylO$_2$SNH—($C_1$-$C_6$)alkylNH— groups;
      ($C_6$)aryl($C_1$-$C_6$)alkyl groups;
      $C_6$ aryl groups;
      ($C_1$-$C_4$)alkylpiperidine groups;
      and the radicals borne by the amino group may form, with the nitrogen atom to which they are attached, a 5- or 6-membered heterocycle optionally comprising a heteroatom chosen from oxygen and nitrogen,
$R_2$, which may be identical or different, is chosen from:
   hydrogen atoms;
   linear or branched $C_1$-$C_6$ alkyl groups, optionally substituted with at least one group chosen from hydroxyl and $C_1$-$C_6$ alkoxy groups;
   $C_5$-$C_6$ cycloalkyl groups optionally substituted with at least one group chosen from hydroxyl and $C_1$-$C_6$ alkoxy groups;
   $C_1$-$C_6$ alkoxy groups;
   halogen atoms;
   cyano groups;
   ($C_6$)aryl($C_1$-$C_6$)alkyl groups; the aryl group being optionally substituted with at least one group chosen from $C_1$-$C_6$ alkyl, hydroxyl and $C_1$-$C_6$ alkoxy groups;
   $C_6$ aryl groups optionally substituted with at least one group chosen from $C_1$-$C_6$ alkyl, hydroxyl and $C_1$-$C_6$ alkoxy groups;
   ($C_1$-$C_6$)alkylcarbonyl groups;
   ($C_1$-$C_6$)alkylcarbonylamino groups;
   ($C_1$-$C_6$)alkylsulfonylamino groups;
   aminocarbonylamino groups;
   ($C_1$-$C_6$)alkylcarbonylamino groups;
   ($C_1$-$C_6$)alkylsulfoamino groups;
   amino groups substituted with one or two radicals, which may be identical or different, chosen from $C_1$-$C_6$ alkyl, $C_1$-$C_6$ hydroxyalkyl and trifluoromethyl radicals;
$R_3$, which may be identical or different, is chosen from:
   hydrogen;
   halogen atoms;
   $C_1$-$C_6$ alkyl groups optionally substituted with at least one group chosen from hydroxyl and $C_1$-$C_6$alkoxy groups;
   $C_1$-$C_6$ alkoxy groups;
   ($C_1$-$C_6$)alkylcarbonylamino groups;

amino groups;
amino($C_1$-$C_6$)alkylcarbonylamino groups;
aminocarbonylamino groups;
($C_1$-$C_6$)alkoxycarbonylamino groups ($C_1$-$C_4$ aminoester alkyl);
aminocarbonyl groups in which the amino group may be mono- or disubstituted with at least one radical, which may be identical or different, chosen from $C_1$-$C_6$alkyl, $C_1$-$C_6$ haloalkyl, ($C_6$)aryl($C_1$-$C_6$)alkyl, $C_6$ aryl, ($C_1$-$C_6$) alkylcarbonylamino and ($C_1$-$C_6$)alkylsulfonylamino radicals, RaCONH— wherein Ra is a $C_1$-$C_4$ haloalkyl group, a ($C_6$)aryl($C_1$-$C_6$)alkyl group, a $C_6$ aryl group, a ($C_1$-$C_6$)alkoxy($C_1$-$C_6$)alkyl group, a $C_1$-$C_6$hydroxyalkyl group, a cyano($C_1$-$C_6$)alkyl group, a methanesulfonamide group, a ($C_1$-$C_6$)alkylamino($C_1$-$C_6$)alkyl group, a substituted or unsubstituted $C_3$-$C_6$ cycloalkenyl group, a β-thienyl group, and one of the following groups:

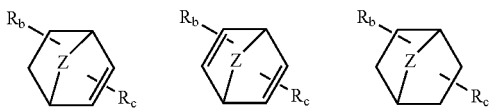

wherein Rb and Rc, independently of each other, are chosen from hydrogen, halogen atoms, and $C_1$-$C_6$ alkyl chains and wherein Z is $CH_2$, O, S or NRd, wherein Rd is chosen from a hydrogen atom and a $C_1$-$C_6$ alkyl chain;
two radicals $R_3$ borne by two adjacent carbon atoms may form a benzene ring optionally substituted with a halogen atom, a $C_1$-$C_6$ alkyl group, an amino group or an amino group mono- or disubstituted with a $C_1$-$C_6$ alkyl or $C_1$-$C_6$ hydroxyalkyl radical;
X is an oxygen atom or an NH group;
an anthraquinone radical of formula (II) below:

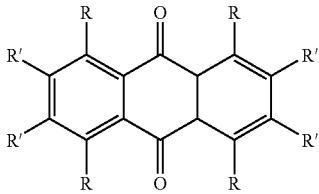

(II)

wherein:
R, independently of each other, are chosen from:
  hydrogen;
  hydroxyl;
  amino groups; and
  amino groups mono- or disubstituted with one or two radicals, which may be identical or different, chosen from $C_1$-$C_6$ alkyl, $C_1$-$C_6$ hydroxyalkyl and $C_6$ aryl radicals optionally substituted with at least one $C_1$-$C_6$ alkyl radical;
R', independently of each other, are chosen from:
  hydrogen;
  halogen;
  hydroxyl;
  amino groups;
  amino groups mono- or disubstituted with one or two radicals, which may be identical or different, chosen from $C_1$-$C_6$ alkyl, $C_1$-$C_6$ alkylamino, $C_5$-$C_8$ cycloalkyl and ($C_1$-$C_6$)alkoxy($C_1$-$C_6$)alkyl radicals;
$C_6$ aryl radicals optionally substituted with at least one group, which may be identical or different, chosen from halogen atoms and $C_1$-$C_6$ alkyl, $C_1$-$C_6$ alkoxy and ($C_1$-$C_6$)alkoxy($C_1$-$C_6$)alkyl radicals;
($C_6$)aryloxy groups;
($C_6$)aryloxy groups substituted with a ($C_6$)aryl-$SO_3$ group, the aryl group being optionally substituted with at least one group, which may be identical or different, chosen from halogen atoms and hydroxyl, trifluoromethyl, $C_1$-$C_6$alkyl, $C_1$-$C_6$ alkoxy, $C_6$ aryl, ($C_6$)aryl($C_1$-$C_4$) alkyl, ($C_6$)aryloxy, nitro, $C_2$-$C_6$ acyl, ($C_2$-$C_6$)acylamino, ($C_1$-$C_6$)alkylmercapto, $C_6$ thiophenyl, sulfonyloxy and ($C_1$-$C_6$)alkylbenzenesulfonyl groups
($C_6$)aryloxy groups substituted with a group —$SO_2N(Ra)_2$ wherein Ra, which may be identical or different, is chosen from a hydrogen atom, a $C_1$-$C_6$ alkyl group, $C_2$-$C_6$ alkenyl group, ($C_6$)aryl($C_1$-$C_6$)alkyl group and a $C_5$-$C_8$ cycloalkyl radical, the two radicals Ra possibly forming, with the nitrogen atom to which they are attached, a 5- or 6-membered heterocycle;
a group —SRb wherein Rb is a 5- or 6-membered heterocycle, comprising the sulfur atom and optionally comprising a nitrogen, sulfur or oxygen atom;
COORc wherein Rc is chosen from a $C_1$-$C_4$ hydroxyalkyl group, ($C_1$-$C_4$)alkylphenyl group, $C_5$-$C_8$ cycloalkyl group, carbonyloxy($C_6$)aryl group and a carbonyl($C_6$) aryl group;
$SO_3$—($C_6$)aryl, the aryl radical being optionally substituted with at least group, which may be identical or different, chosen from halogen atoms and hydroxyl, trifluoromethyl, $C_1$-$C_6$ alkyl, $C_1$-$C_6$ alkoxy, $C_6$ aryl, ($C_6$) aryl($C_1$-$C_4$)alkyl, ($C_6$)aryloxy, nitro, $C_2$-$C_6$ acyl, ($C_2$-$C_6$)acylamino, ($C_1$-$C_6$)alkylmercapto, thiophenyl, sulfonyloxy and ($C_1$-$C_6$)alkyl-benzenesulfonyl groups.
an azo dye corresponding to formula (III) below:

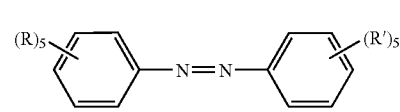

(III)

wherein:
R, which may be identical or different, and R', which may be identical or different, independently of each other, are chosen from:
  hydrogen;
  linear, branched or cyclic, saturated, unsaturated or aromatic $C_1$-$C_{30}$ hydrocarbon-based chains, optionally substituted with at least one halogen atom or with at least one group, which may be identical or different, chosen from the following groups: hydroxyl; nitro; cyano; carboxylic acid; allyl; haloallyl; $C_1$-$C_{10}$ alkoxy; ($C_1$-$C_4$) alkylcarbonylamino; ($C_1$-$C_4$)alkylaminocarbonyl; hydrogeno-carbonylamino; ($C_1$-$C_4$)alkylsulfonylamino; ($C_1$-$C_4$)alkoxycarbonylamino; ($C_1$-$C_4$)alkoxycarbonyl; ($C_1$-$C_4$)alkylcarbonyl($C_1$-$C_4$)alkoxycarbonyl; $CF_3$; amino; amino optionally substituted with at least one group, which may be identical or different, chosen from $C_1$-$C_{10}$ alkyl, $C_1$-$C_{10}$ hydroxyalkyl, $C_1$-$C_{10}$ alkoxyalkyl, $C_1$-$C_{10}$ aminoalkyl, (di)($C_1$-$C_{10}$)alkylamino($C_1$-$C_{10}$)alkyl, cyano($C_1$-$C_{10}$)alkyl, $C_6$-$C_{30}$ aryl, ($C_6$-$C_{30}$)aryl($C_1$-$C_4$)alkyl, ($C_4$-$C_{30}$)cyclo($C_1$-$C_{12}$)alkyl, ($C_1$-$C_4$)alkylcarbonyl, ($C_1$-$C_4$)alkylcarboxy($C_1$-$C_4$) alkyl, allyl, haloallyl; and optionally interrupted with or attached to the aromatic nucleus via at least one heteroatom or via a group comprising at least one heteroatom chosen from oxygen, sulfur and nitrogen;

groups chosen from: hydroxyl; $C_1$-$C_4$ alkoxy; carboxylic acid; amino; amino substituted with at least one radical, which may be identical or different, chosen from $C_1$-$C_4$ alkyl, $C_2$-$C_4$ alkenyl, cyano($C_1$-$C_4$)alkyl, $C_1$-$C_4$ hydroxyalkyl, $C_6$-$C_{30}$ aryl, ($C_6$-$C_{30}$)aryl($C_1$-$C_4$)alkyl, allyl, ($C_1$-$C_4$)alkoxy($C_1$-$C_4$)alkyl, ($C_4$-$C_{30}$)cyclo($C_1$-$C_{12}$)alkyl, ($C_1$-$C_4$)alkylcarbonyl, ($C_1$-$C_4$)carboxy($C_1$-$C_4$)alkyl, haloallyl, amino($C_1$-$C_4$)alkyl, (di)($C_1$-$C_4$)alkylamino($C_1$-$C_4$)alkyl, ($C_1$-$C_4$)alkylsulfonyl, ($C_1$-$C_4$) alkoxycarbonyl; halogen; allyl; hydrogenocarbonyl; trifluoromethyl; nitro; and cyano radicals it being understood that at least one of the radicals R or R' is a group chosen from hydroxyl; nitro; cyano; amino; amino optionally substituted with one or more radicals; and optionally, two radicals R borne by two adjacent carbon atoms or two radicals R' borne by two adjacent carbon atoms may form, with the aromatic ring bearing the carbon atoms to which each is attached, a fused nucleus of naphthalene type optionally substituted with an aminosulfonyl or ($C_1$-$C_4$)alkylaminosulfonyl group.

12. The cosmetic article according to claim 11, wherein the radical $R_1$ of formula (I) is chosen from:

a hydroxyl group;

an amino group;

an amino group mono- or disubstituted with one or two radicals, which may be identical or different, chosen from: $C_1$-$C_4$ alkyl optionally substituted with a ($C_1$-$C_4$) alkylSO$_2$NH group or an NH$_2$CO— group; the radicals borne by the amino group may form, with the nitrogen atom to which they are attached, a 5- or 6-membered heterocycle optionally comprising a heteroatom chosen from oxygen and nitrogen.

13. The cosmetic article according to claim 11, wherein the radicals $R_2$ of formula (I), which may be identical or different, are chosen from:

hydrogen;

linear or branched $C_1$-$C_4$ alkyl groups;

$C_1$-$C_4$ alkoxy groups; and halogen atoms.

14. The cosmetic article according to claim 11, wherein the radicals $R_3$ of formula (I), which may be identical or different, are chosen from:

hydrogen;

$C_1$-$C_6$ alkyl groups optionally substituted with at least one group chosen from hydroxyl and $C_1$-$C_6$ alkoxy groups;

$C_1$-$C_4$ alkoxy groups;

amino groups;

($C_1$-$C_6$)alkylcarbonylamino groups;

($C_1$-$C_4$)alkoxycarbonylamino groups;

two radicals $R_3$ borne by two adjacent carbon atoms may form a benzene ring optionally substituted with a halogen atom, a $C_1$-$C_6$ alkyl group, an amino group or an amino group mono- or disubstituted with a $C_1$-$C_6$ alkyl or $C_1$-$C_6$ hydroxyalkyl radical.

15. The cosmetic article according to claim 11, wherein the anthraquinone direct dye corresponds to formula (IIa) below:

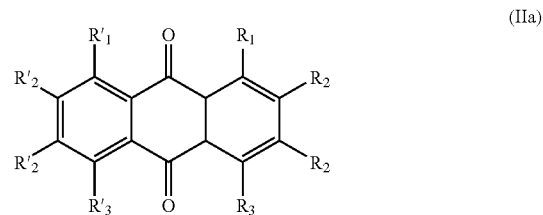

(IIa)

wherein:

$R_1$ is chosen from a hydrogen atom, a hydroxyl group, an amino group, and an amino group mono- or disubstituted with one or two radicals, which may be identical or different, chosen from $C_1$-$C_4$ alkyl, $C_1$-$C_6$ hydroxyalkyl and phenyl radicals optionally substituted with at least one $C_1$-$C_4$ alkyl radical;

$R'_1$ is chosen from a hydrogen atom, a hydroxyl group and an amino group;

$R_2$ and $R'_2$, independently of each other, may be chosen from hydrogen;

halogen atoms;

hydroxyl groups;

amino groups;

amino groups mono- or disubstituted with one or two radicals, which may be identical or different, chosen from $C_1$-$C_6$ alkyl, $C_1$-$C_6$ alkylamino, $C_5$-$C_8$ cycloalkyl and ($C_1$-$C_6$)alkoxy($C_1$-$C_6$)alkyl radicals;

$C_6$ aryl radicals optionally substituted with at least one group, which may be identical or different, chosen from halogen atoms and $C_1$-$C_6$ alkyl, $C_1$-$C_6$alkoxy and ($C_1$-$C_6$)alkoxy($C_1$-$C_6$)alkyl radicals;

($C_6$)aryloxy groups;

$R_3$ is chosen from a hydrogen atom, a hydroxyl group, an amino group, an amino group mono- or disubstituted with one or two radicals, which may be identical or different, chosen from $C_1$-$C_6$ alkyl, $C_1$-$C_6$ hydroxyalkyl and $C_6$ aryl radicals optionally substituted with one or more $C_1$-$C_6$ alkyl radicals;

$R'_3$ is chosen from a hydrogen atom, a hydroxyl group, and an amino group.

16. The cosmetic article according to claim 15, wherein the anthraquinone direct dye of formula (IIa) is chosen from the following direct dyes: Disperse Blue 1 [2475-45-8], Disperse Blue 3 [2475-46-9], Disperse Blue 14 [2475-44-7], Disperse Blue 19 [4395-65-7], Disperse Blue 26 [3860-63-7], Disperse Blue 56 [31810-89-6], Disperse Orange 11 [82-28-0], Disperse Red 60 [17418-58-5], Disperse Violet 1 [128-95-0], Solvent Blue 35 [17354-14-2], Solvent Blue 59 [6994-46-3], Solvent Green 3 [17418-58-5], 6-methyl-1,3,8-trihydroxyanthraquinone (Emodine) [518-82-1], purpurin [81-54-9], quinalizarin [81-61-8], and mixtures thereof.

17. The cosmetic article according to claim 11, wherein the azo direct dye corresponds to formula (IIIa) below:

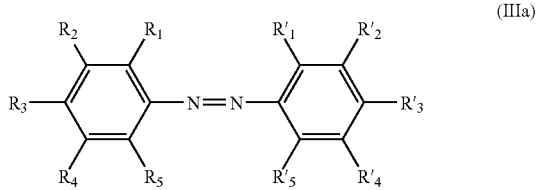

(IIIa)

wherein:
- R'$_1$ is chosen from a hydrogen atom, an amino group and a hydroxyl group;
- R'$_2$ is chosen from a hydrogen atom, a halogen atom, a carboxylic acid group, a $C_1$-$C_4$ alkyl group, a $C_1$-$C_4$ alkoxy group, an allyl group and an aminocarbonyl($C_1$-$C_4$)alkyl group;
- R'$_3$ is chosen from a hydrogen atom, a hydroxyl group and a group of the type NR'$_1$R'$_2$ wherein R'$_1$ and R'$_2$ are chosen from, independently of each other, a hydrogen atom, a $C_1$-$C_4$ alkyl group, a $C_2$-$C_4$ alkenyl group, a cyano($C_1$-$C_4$)alkyl group, a $C_1$-$C_4$ hydroxyalkyl group, a $C_6$-$C_{30}$ aryl group, a ($C_6$-$C_{30}$)aryl($C_1$-$C_4$)alkyl group, an allyl group, a ($C_1$-$C_4$)alkoxy($C_1$-$C_4$)alkyl group, a ($C_4$-$C_{30}$)cyclo($C_1$-$C_{12}$)alkyl group, a ($C_1$-$C_4$)alkylcarbonyl group, a ($C_1$-$C_4$)alkylcarboxy($C_1$-$C_4$)alkyl group or a haloallyl group, a $C_1$-$C_4$ aminoalkyl group and a (di)($C_1$-$C_4$)alkylamino($C_1$-$C_4$)alkyl group;
- R'$_2$ and R'$_3$ may form, with the benzene nucleus, a fused nucleus of naphthalene type optionally substituted with a group —SO$_2$—NHR wherein R is a hydrogen atom or an optionally substituted $C_1$-$C_4$ alkyl chain;
- R'$_4$ is chosen from a hydrogen atom, a halogen atom, a hydroxyl group, a $C_1$-$C_4$ alkyl group, a $C_1$-$C_4$ alkoxy group and a ($C_1$-$C_4$)alkoxy($C_1$-$C_4$)alkyl group;
- R'$_5$ is chosen from a hydrogen atom, a halogen atom, a hydroxyl group, an amino group, a $C_1$-$C_4$ alkyl group, a $C_1$-$C_4$ alkoxy group, a ($C_1$-$C_4$)alkylcarbonylamino group, a hydrogenocarbonylamino group, ($C_1$-$C_4$)alkylsulfonylamino, a ($C_1$-$C_4$)alkoxycarbonylamino group and a CF$_3$ group;
- R'$_4$ and R'$_5$ may form, with the benzene nucleus, a fused nucleus of naphthalene type;
- R$_1$ is chosen from a hydrogen atom, a halogen atom, a hydroxyl group, a nitro group and a cyano group;
- R$_2$ is chosen from a hydrogen atom, a nitro group and a $C_1$-$C_4$ alkyl group;
- R$_3$ is chosen from a hydrogen atom, a $C_1$-$C_4$ alkyl group, a $C_1$-$C_4$ alkoxy group, a ($C_4$-$C_{30}$)cyclo($C_1$-$C_{12}$)alkyl group, a $C_2$-$C_4$ alkenyl group, a ($C_1$-$C_4$)alkoxycarbonyl group, a ($C_1$-$C_4$)alkylcarbonyl group, a ($C_1$-$C_4$)alkoxycarbonyl($C_1$-$C_4$)alkoxycarbonyl group, ($C_1$-$C_4$)alkylcarbonyl($C_1$-$C_4$)alkoxycarbonyl, an aryl group, an amino group, a nitro group, a cyano group and a CF$_3$ group;
- R$_4$ is a hydrogen atom or a nitro group;
- R$_5$ is chosen from a hydrogen atom, a halogen atom, a carboxylic acid group, a hydroxyl group, an amino group, a cyano group and a $C_1$-$C_4$ alkyl group;
- it being understood that at least one of the radicals R'$_1$ to R'$_5$ and R$_1$ to R$_5$ is a group chosen from hydroxyl, nitro, cyano, amino, amino optionally substituted with at least one radical.

18. The cosmetic article according to claim 17, wherein, in formula (IIIa): the radicals R'$_1$, R'$_2$, R$_1$, R$_2$ and R$_4$ are each a hydrogen atom; and/or
- the radical R'$_3$ is chosen from a hydrogen atom and NR"$_1$R"$_2$ wherein R"$_1$ and R"$_2$ are chosen from, independently of each other, hydrogen, $C_1$-$C_4$ alkyl groups, cyano($C_1$-$C_4$)alkyl groups, $C_1$-$C_4$ hydroxyalkyl groups and $C_1$-$C_4$ aminoalkyl groups; and/or
- the radical R'$_4$ is a hydrogen atom and the radical R'$_5$ is chosen from a hydrogen atom and a $C_1$-$C_4$ alkyl group; or the radicals R'$_4$ and R'$_5$ form, with the benzene nucleus, a fused nucleus of naphthalene type; and/or
- the radical R$_3$ is chosen from an amino group and a nitro group; and
- the radical R$_5$ is chosen from a hydrogen atom, a halogen atom, and an amino group.

19. The cosmetic article according to claim 17 wherein the azo direct dye of formula (IIIa) is chosen from the following direct dyes: Solvent Brown 1 [6416-57-5], Solvent Orange 1 [2051-85-6], Solvent Orange 7 [3118-97-6], Solvent Yellow 2 [60-11-7], Solvent Yellow 3 [97-56-3], Solvent Yellow 7 [1689-82-3], Solvent Yellow 14 [842-07-9], Disperse Orange 1 [2581-69-3], Disperse Orange 3 [730-40-5], Disperse Orange 25 [31482-56-1], Disperse Red 1 [2872-52-8], Disperse Red 13 [3180-81-2], Disperse Red 19 [2734-52-3], Disperse Red 50 [12223-35-7]+[40880-51-1], Disperse Yellow 3, Mordant Brown 4 [6247-28-5], Mordant Brown 6 [6247-28-5], Mordant Brown 24 [6370-46-3], Mordant Brown 48 [6232-53-7], Mordant Orange 1 [2243-76-7], Pigment Red 3 [2425-85-6], 4-dimethylamino-2-methylazobenzene [54-88-6], 2-(4-diethylaminophenylazo)benzoic acid [76058-33-8], N-ethyl-N-(2-aminoethyl)-4-(4-nitrophenylazo)aniline, N,N-hydroxyethyl-4-(4-nitrophenylazo)-2-methylaniline, N,N-hydroxyethyl-4-(4-aminophenylazo)-2-aniline, and mixtures thereof.

20. The cosmetic article according to claim 1, wherein the direct dye(s) or direct dye precursor(s) are present in an amount ranging from 0.5% to 50% by weight relative to the total weight of the cosmetic article.

21. A process for dyeing keratin materials, comprising
- positioning a cosmetic article on or close to the keratin materials, wherein said cosmetic article is substantially dry and comprises:
  - a porous flexible substrate chosen from nonwoven fibrous substrates and cellular substrates of foam type, and
  - at least one direct dye and/or direct dye precursor in powder form and capable of dyeing the keratin material via heat transfer,
  - wherein the substrate and the at least one direct dye and/or direct dye precursor are non-covalently bonded to and/or in the substrate, and
- applying a source of heat, resulting in thermal transfer of the dye(s) onto or into the keratin materials.

22. The process according to claim 21, wherein the source of heat is at a temperature ranging from 100 to 500° C.

23. The process according to claim 21, wherein the time for applying the source of heat ranges from 1 second to 5 minutes.

* * * * *

UNITED STATES PATENT AND TRADEMARK OFFICE
CERTIFICATE OF CORRECTION

PATENT NO.         : 7,611,545 B2
APPLICATION NO. : 12/000598
DATED                : November 3, 2009
INVENTOR(S)       : Frédéric Guerin et al.

It is certified that error appears in the above-identified patent and that said Letters Patent is hereby corrected as shown below:

On the title page, item (57), line 3, "dyes" should read --dye--.

In claim 10, column 13, lines 62-63, "isoindoline, isoindoline, isoindolinone," should read --isoindoline, isoindolinone,--.

In claim 11, column 15, lines 21-24,

" 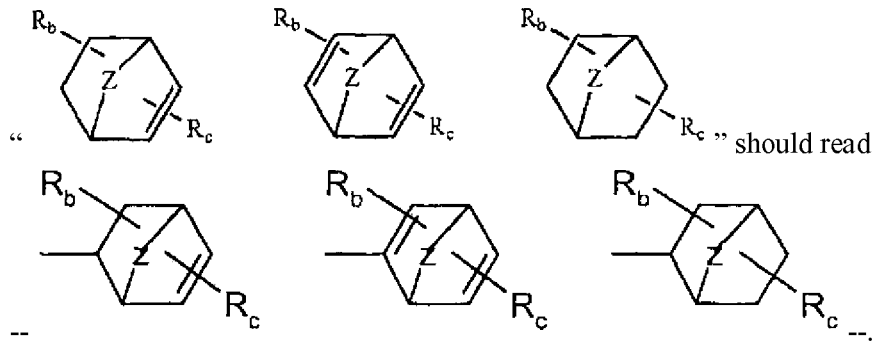 " should read -- 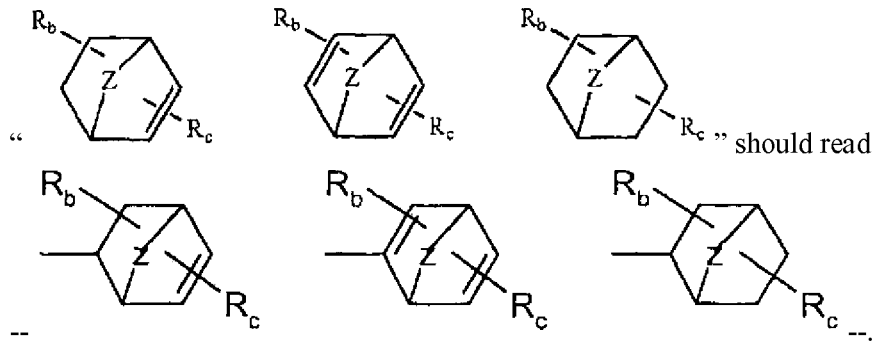 --.

In claim 11, column 16, line 29, "least group," should read --least one group,--.

In claim 11, column 16, line 34, "groups." should read --groups;--.

Signed and Sealed this

Twenty-ninth Day of December, 2009

David J. Kappos
*Director of the United States Patent and Trademark Office*